United States Patent  
Kato et al.

(10) Patent No.: US 10,338,012 B2  
(45) Date of Patent: Jul. 2, 2019

(54) PHOTON COUNTING DETECTOR AND X-RAY COMPUTED TOMOGRAPHY (CT) APPARATUS

(71) Applicant: Toshiba Medical Systems Corporation, Otawara-shi (JP)

(72) Inventors: Tooru Kato, Nasushiobara (JP); Hiroaki Nakai, Nasushiobara (JP); Mikihito Hayashi, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 15/446,325

(22) Filed: Mar. 1, 2017

(65) Prior Publication Data

US 2017/0261620 A1 Sep. 14, 2017

(30) Foreign Application Priority Data

Mar. 9, 2016 (JP) .................................. 2016-045781  
Feb. 20, 2017 (JP) .................................. 2017-028730

(51) Int. Cl.
  *G01T 1/17* (2006.01)  
  *G01N 23/046* (2018.01)

(52) U.S. Cl.
  CPC ............. *G01N 23/046* (2013.01); *G01T 1/17* (2013.01); *G01T 1/171* (2013.01)

(58) Field of Classification Search
  CPC ......... G01T 1/18; G01T 1/2018; G01T 1/247; G01T 1/249; G01N 23/046  
  USPC .............................. 250/208.1, 370.08, 370.09  
  See application file for complete search history.

(56) References Cited

U.S. PATENT DOCUMENTS

| | | | | |
|---|---|---|---|---|
| 3,344,278 A * | 9/1967 | Yanai | .................. | H01L 27/0817 250/569 |
| 4,075,490 A * | 2/1978 | Kowalski | ............... | A61B 6/032 378/4 |
| 5,591,960 A * | 1/1997 | Furukawa | ......... | H01L 27/14643 250/201.8 |
| 5,812,191 A * | 9/1998 | Orava | .................. | G01T 1/2928 348/308 |
| 6,448,559 B1* | 9/2002 | Saoudi | .................. | G01T 1/1603 250/367 |
| 6,788,812 B1* | 9/2004 | Wilkins | .................. | G06T 5/008 345/22 |

(Continued)

FOREIGN PATENT DOCUMENTS

JP 9-5445 A 1/1997  
JP 2013-90233 A 5/2013

(Continued)

*Primary Examiner* — David P Porta  
*Assistant Examiner* — Blake C Riddick  
(74) *Attorney, Agent, or Firm* — Oblon, McClelland, Maier & Neustadt, L.L.P.

(57) ABSTRACT

A photon counting detector of an embodiment includes X-ray detection elements, a capacitor, and generating circuitry. The X-ray detection elements detect an X-ray and generate an electrical signal. The capacitor is provided for each of the X-ray detection element, and accumulates an electrical signal generated in each of the X-ray detection element. The generating circuitry has low sensitivity to radiation, and generates a digital signal by using an accumulation result of the electrical signal in the capacitors, and reference information that is stored in advance.

21 Claims, 12 Drawing Sheets

(56) References Cited

U.S. PATENT DOCUMENTS

| | | | |
|---|---|---|---|
| 8,350,221 B2 * | 1/2013 | Steadman Booker | G01T 1/17 250/336.1 |
| 8,493,483 B2 | 7/2013 | Nishihara | |
| 8,754,378 B2 | 6/2014 | Prescher et al. | |
| 8,953,072 B2 | 2/2015 | Nishihara | |
| 9,055,244 B2 | 6/2015 | Nishihara | |
| 9,227,154 B2 | 1/2016 | Yoshizumi et al. | |
| 9,369,650 B2 | 6/2016 | Nishihara | |
| 2004/0017224 A1 * | 1/2004 | Turner | H03F 3/087 327/51 |
| 2004/0212708 A1 * | 10/2004 | Spartiotis | H04N 5/32 348/295 |
| 2007/0053564 A1 * | 3/2007 | Matsumoto | G06T 7/0012 382/128 |
| 2007/0092067 A1 * | 4/2007 | Fujisawa | A61B 6/032 378/196 |
| 2009/0121142 A1 * | 5/2009 | Heismann | G01T 1/2018 250/363.04 |
| 2010/0010343 A1 * | 1/2010 | Daghighian | A61B 6/037 600/436 |
| 2010/0204942 A1 * | 8/2010 | Danielsson | G01T 1/242 702/85 |
| 2010/0329425 A1 * | 12/2010 | Guo | G01T 1/247 378/91 |
| 2011/0036989 A1 * | 2/2011 | Marks | G01T 1/17 250/370.08 |
| 2011/0168909 A1 | 7/2011 | Nakao et al. | |
| 2011/0210235 A1 * | 9/2011 | Dierickx | G01T 1/17 250/214 R |
| 2012/0057059 A1 * | 3/2012 | Eldesouki | H01L 27/14601 348/302 |
| 2012/0057152 A1 * | 3/2012 | Eldesouki | G01J 1/46 356/226 |
| 2014/0105370 A1 * | 4/2014 | Yamakawa | A61B 6/025 378/207 |
| 2014/0293107 A1 | 10/2014 | Nishihara et al. | |
| 2015/0076325 A1 * | 3/2015 | Higuchi | H04N 5/357 250/208.1 |
| 2015/0081262 A1 * | 3/2015 | Yahil | G06F 17/18 703/2 |
| 2015/0195470 A1 * | 7/2015 | Millet | H04N 5/335 348/308 |
| 2015/0327827 A1 * | 11/2015 | Teshigawara | A61B 6/032 378/19 |
| 2016/0191830 A1 | 6/2016 | Nishihara et al. | |
| 2016/0241805 A1 | 8/2016 | Nishihara | |

FOREIGN PATENT DOCUMENTS

| | | |
|---|---|---|
| JP | 5569314 B2 | 8/2014 |
| WO | WO 2010/035671 A1 | 4/2010 |

* cited by examiner

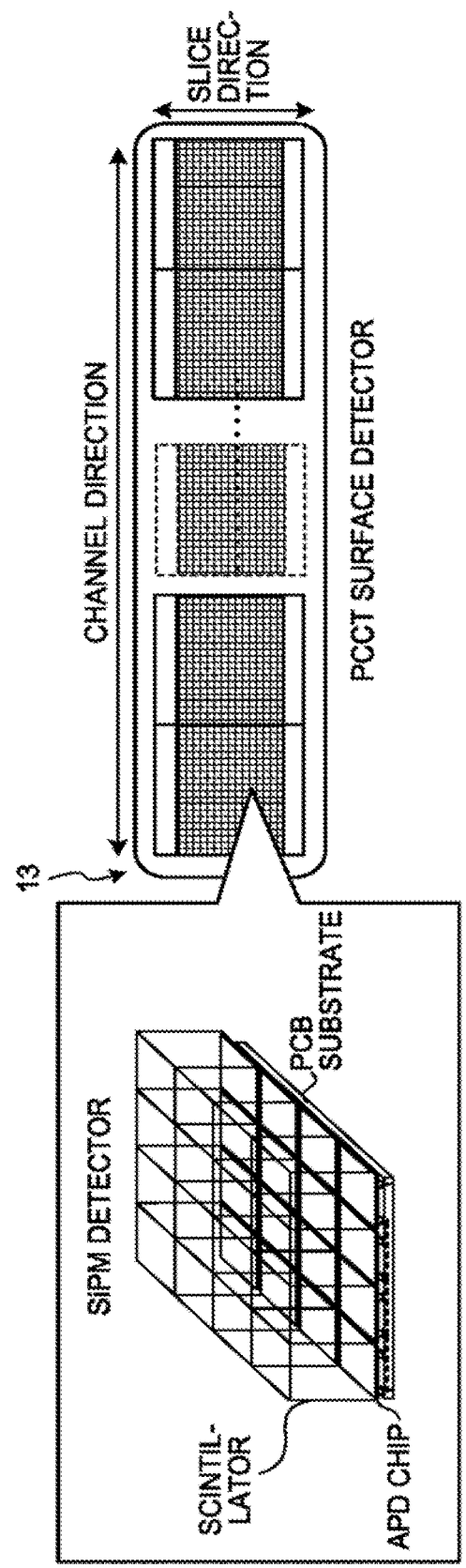

US 10,338,012 B2

PHOTON COUNTING DETECTOR AND X-RAY COMPUTED TOMOGRAPHY (CT) APPARATUS

CROSS-REFERENCE TO RELATED APPLICATIONS

This application is based upon and claims the benefit of priority from Japanese Patent Application No. 2016-045781, filed on Mar. 9, 2016 and No. 2017-028730, filed on Feb. 20, 2017; the entire contents of which are incorporated herein by reference.

FIELD

Embodiments described herein relate generally to a photon counting detector and an X-ray CT apparatus.

BACKGROUND

As an X-ray detector used in an X-ray CT apparatus, a photon-counting X-ray detector has been known. The photon-counting X-ray detector detects each of incident X-ray beams as a photon, and counts the number of photons, thereby measuring the intensity of an X-ray. Moreover, as an electric charge is generated in an amount according to an energy of an X-ray photon when the X-ray photon is converted into an electric charge, the photon-counting X-ray detector measures an energy of each X-ray photon. Therefore, the photon-counting X-ray detector can measure also an energy spectrum of an X-ray beam.

BRIEF DESCRIPTION OF THE DRAWINGS

FIG. 2E is a diagram for explaining the detector according to the first embodiment;

DETAILED DESCRIPTION

A photon counting detector and an X-ray CT apparatus according to embodiments are explained below with reference to the drawings. Embodiments are not limited to the embodiments below. Furthermore, what is described in one embodiment can be similarly applied to another embodiment in principle.

An X-ray CT apparatus explained in the following embodiment is an apparatus capable of performing photon counting CT. That is, the X-ray CT apparatus explained in the following embodiment is an apparatus that is capable of reconstructing X-ray CT image data with a high signal-to-noise (S/N) ratio by counting X-ray beams that have passed through a subject body not by using a conventional integral (current-mode measuring) detector, but by using a photon counting detector.

A photon counting detector of an embodiment includes X-ray detection elements, a capacitor, and generating circuitry. The X-ray detection elements detect an X-ray and generate an electrical signal. The capacitor is provided for each of the X-ray detection element, and accumulates an electrical signal generated in each of the X-ray detection element. The generating circuitry has low sensitivity to radiation, and generates a digital signal by using an accumulation result of the electrical signal in the capacitors, and reference information that is stored in advance.

First Embodiment

Figure 1:
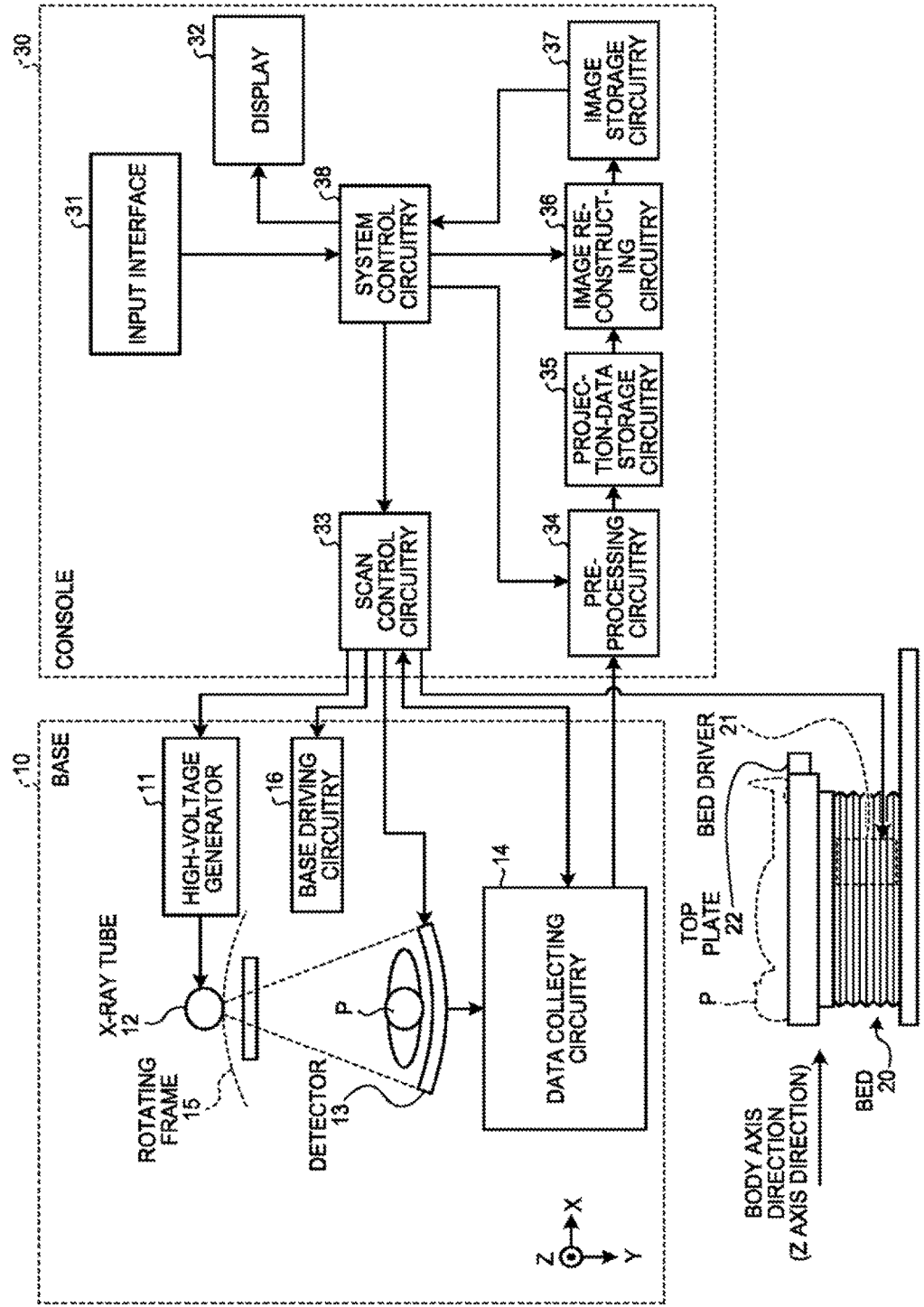
FIG. 1 shows a configuration example of an X-ray CT apparatus according to a first embodiment.

FIG. 1 shows a configuration example of an X-ray CT apparatus according to a first embodiment. As shown in FIG. 1, the X-ray CT apparatus according to the first embodiment includes a base 10, a bed 20, and a console 30.

The base 10 is a device that irradiates a subject P with an X-ray, and that collects data relating to an X-ray that has passed through the subject P, and includes a high-voltage generator 11, an X-ray tube 12, a detector 13, data collecting circuitry 14, a rotating frame 15, and base driving circuitry 16.

The rotating frame 15 is an annular frame that supports the X-ray tube 12 and the detector 13 so as to oppose to each other sandwiching the subject P in between, and that is rotated by the base driving circuitry 16 to be described later, along an orbit around the subject P in center thereof at a high speed.

The X-ray tube 12 is a vacuum tube that irradiates the subject P with an X-ray beam by high voltage supplied by the high-voltage generator 11 described later, and irradiates the subject P with an X-ray beam as rotation of the rotating frame 15. The X-ray tube 12 is an X-ray source that radiates an X-ray.

The high-voltage generator 11 is a device that supplies a high voltage to the X-ray tube 12, and generates an X-ray by using the high voltage supplied by the high-voltage generator 11. That is, the high-voltage generator 11 adjusts an amount of X-ray to be irradiated to the subject P by adjusting a tube voltage and a tube current to be supplied to the X-ray tube 12.

The base driving circuitry 16 rotates the X-ray tube 12 and the detector 13 along an orbit around the subject P in center by driving the rotating frame 15 to be rotated.

The detector 13 has plural detecting devices that detect an X-ray that has passed through the subject P and generate an electrical signal. The detector 13 is explained by using FIG. 2A to FIG. 2E. FIG. 2A to FIG. 2E are diagrams for explaining the detector 13 according to the first embodiment.

Figure 2A:
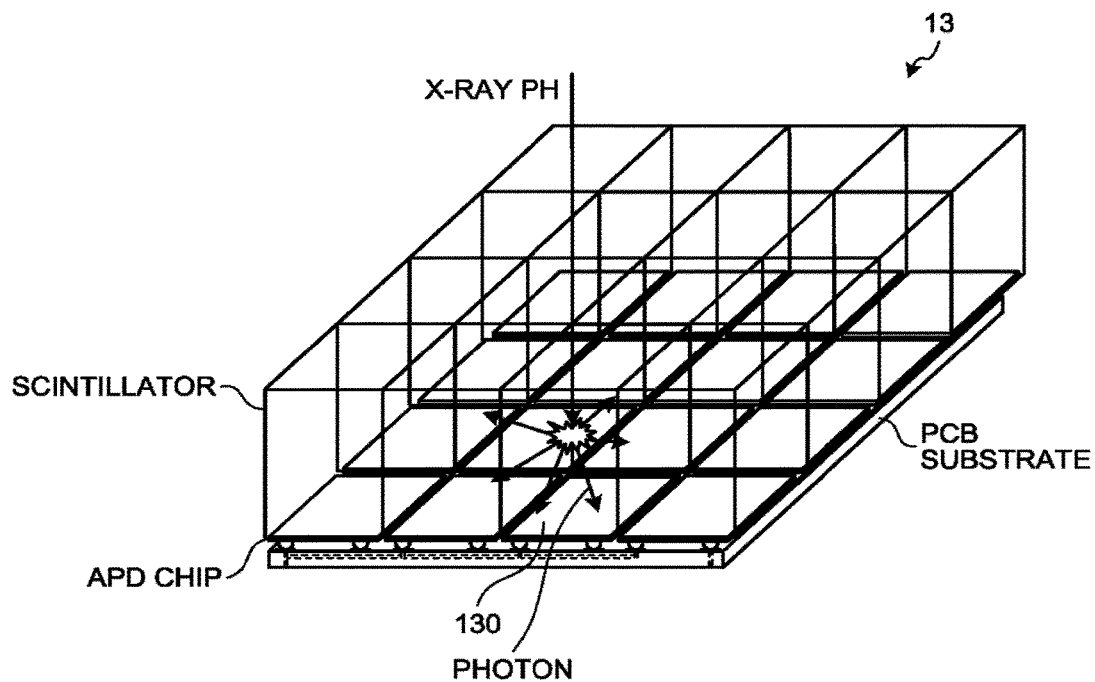
FIG. 2A is a diagram for explaining a detector according to the first embodiment.

The detecting device included in the detector 13 is explained by using FIG. 2A. FIG. 2A shows 16 pieces of the detecting devices that are arranged in four rows by four columns, out of the detecting devices included in the detector 13. As shown in FIG. 2A, the detecting devices included in the detector 13 according to the first embodiment are an indirect conversion detector that is constituted of a scintillator and an optical sensor.

The scintillator converts an incident X-ray that is radiated from the X-ray source into a scintillator light. This scintillator light is constituted of photons in quantity according to an energy of an incident X-ray. In the scintillator, a silicon photomultiplier (SiPM) 130 as an optical sensor is arranged at an end on a side opposing to a side of an X-ray incident direction. The SiPM arranged in each scintillator constitutes one pixel. Therefore, the SiPM 130 is also referred to as one pixel.

The SiPM 130 according to the first embodiment has an avalanche photo diode (APD) cell 140 that includes plural APDs 141 each of which operates independently. Generally, in one pixel, several hundreds to several thousands of APDs are arranged. In the example shown in FIG. 2B, 72 pieces of APDs 141 that are arranged in nine rows by eight columns are illustrated, out of the APDs 141 included in the APD cell 140. Moreover, the APD 141 is also referred to as a photoelectric converter.

Figure 2B:
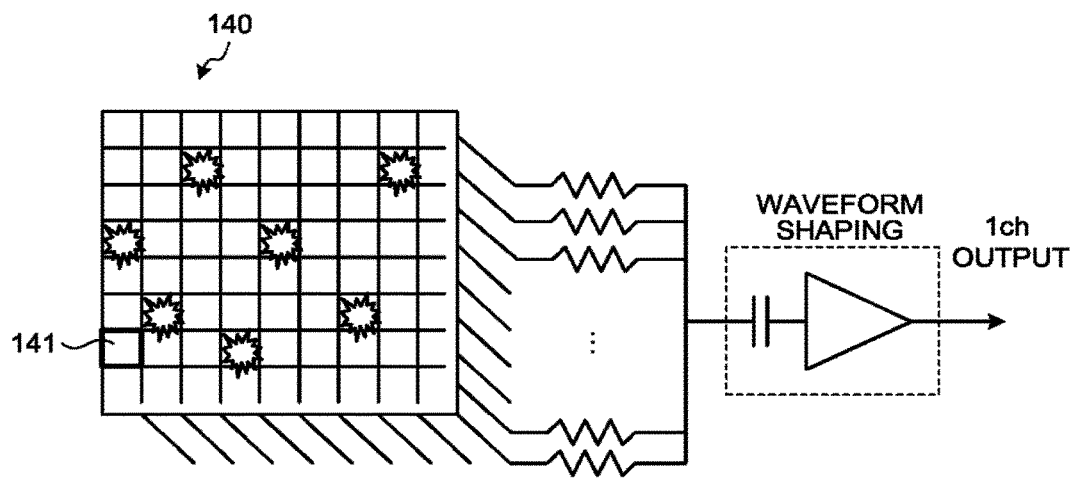
FIG. 2B is a diagram for explaining the detector according to the first embodiment.
Figure 2C:
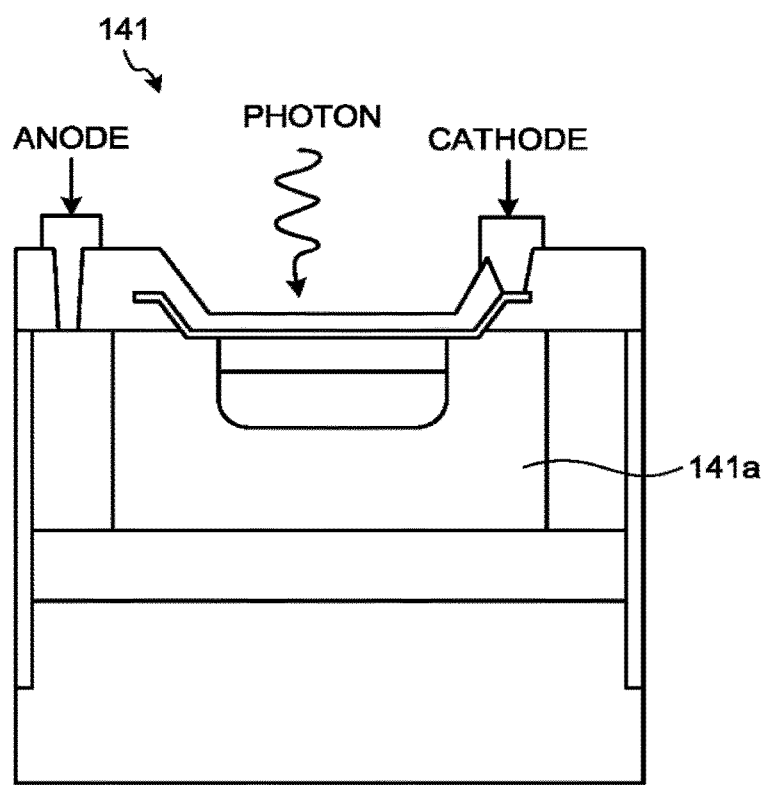
FIG. 2C is a diagram for explaining the detector according to the first embodiment.

The APD 141 is a photodiode including an avalanche region 141a as shown in FIG. 2C, and is a photodiode that uses the avalanche multiplication effect of multiplying a photocurrent by applying a reverse bias. By the avalanche multiplication effect, an electron of an electron hole pair generated in a depletion layer flows to an N layer and a positive hole thereof flows to a P layer when an inverse voltage is applied to a PN junction, and a part of electrons and positive holes collide with another atom to form a new electron hole pair. These electron and positive hole further collide with an atom to form another new electron hole pair. Thus, a chain reaction occurs. That is, more electron hole pairs are generated in the APD 141 than electron hole pairs generated by an incident light. As described, the APD 141 is a highly sensitive photodiode that generates a high output even with a weak light.

Explanation returns to FIG. 2B. In the APD cell 140, the APDs 141 of the number of cells proportional to the energy of the incident X-ray ignite. In other word, in the APD cell 140, the APDs 141 of the number of cells proportional to the energy of the incident X-ray makes signal current. For example, in the APD cell 140, each of the ignited APDs 141 detects one photon and outputs a signal. The APD cell 140 outputs the total of the signals output by the entire APDs 141 in the APD cell 140 as an output signal of one pixel.

Figure 2D:
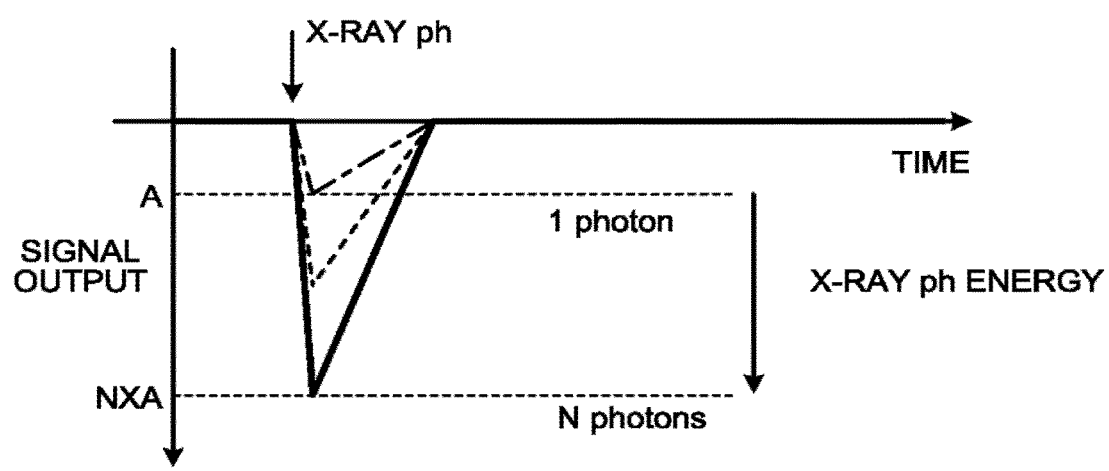
FIG. 2D is a diagram for explaining the detector according to the first embodiment.

More specifically, each of the APDs 141 in the APD cell 140 outputs the same pulse when detecting one photon. Therefore, the APD cell 140 outputs an output signal corresponding to the total number of the APDs 141 that have detected a photon. For example, an output signal when one photon is detected is A. The APD cell 140 outputs the output signal A when one photon is detected, as shown in FIG. 2D, and outputs an output signal n×A when n pieces of photons are detected. As described, the APD cell 140 outputs an output signal corresponding to the total number of the APDs 141 that have detected a photon. In other words, the APD cell 140 outputs an output signal corresponding to the energy of an X-ray.

Moreover, the detector 13 is a surface detector on which SiPMs are arranged in multiple lines in a channel direction and a slice direction as shown in FIG. 2E. As the number of columns in the slice direction increases, an area of an image collectable in a single rotation increases. The number of pixels of the detector 13 can be of an arbitrary number, but as one example, it is explained assuming that it is about 8000 pixels. For example, the detector 13 captures images at 3000 (views/second). When the detector 13 rotates three times in 1 second, the number of views to be captured is about 1000 views at 1 rotation.

Returning to FIG. 1, the data collecting circuitry 14 collects a counting result that is a result of counting processing using the output signal of the detector 13. The data collecting circuitry 14 counts photons (X-ray photons) derived from an X-ray that has been irradiated from the X-ray tube 12 and has passed through the subject P, and collects a result of discrimination of an energy of the counted photons as the counting result. The data collecting circuitry 14 then transmits the counting result to the console 30.

Specifically, the data collecting circuitry 14 collects an incident position (detection position) of X-ray photons that are counted by discriminating each pulse output by the detecting device, and an energy value of the X-ray photon as a counting result per phase (vacuum phase) of the X-ray tube 12. The data collecting circuitry 14 regards, for example, a position of the detecting device that has output a pulse used for counting as the incident position. Moreover, the data collecting circuitry 14 calculates the energy value, for example, from a peak value of the pulse and a system-specific response function. Alternatively, the data collecting circuitry 14 calculates the energy value by integrating the intensity of the pulse. The data collecting circuitry 14 distributes calculated energy values (E) to plural energy discrimination ranges.

The data collecting circuitry 14 according to the present embodiment distributes calculated energy values to plural energy discrimination ranges, for example, by using a comparator. The energy discrimination ranges are to be an energy division set determined using thresholds for the data collecting circuitry 14 to distribute an energy value to an energy range of a predetermined particle size.

For example, the counting result collected by the data collecting circuitry 14 is to be information indicating that "in a vacuum phase "α1", a count value of photons of an energy discrimination range "E1<E≤E2" is "N1", and a count value of photons of an energy discrimination range "E2<E≤E3" is "N2" at a detecting device at an incident position "P11".

Alternatively, the counting result collected by the data collecting circuitry 14 is to be information indicating that in the vacuum phase "α1", a count value of photons per unit time of the energy discrimination range "E1<E≤E2" is "n1" and a count value of photons per unit time of the energy discrimination range "E2<E≤E3" is "n2" at the detecting device at the incident position "P11".

The bed 20 is a device on which the subject P is placed, and includes a top plate 22 and a bed driver 21. The top plate 22 is a plate on which the subject P is laid, and the bed driver 21 moves the top plate 22 in a Z axis direction to move the subject P into the rotating frame 15.

The base 10 performs, for example, helical scanning in which the subject P is scanned in a spiral by rotating the rotating frame 15 while moving the top plate 22. Alternatively, the base 10 performs conventional scanning in which the subject P is scanned in a circular orbit by rotating the rotating frame 15 fixing the position of the subject P after the top plate 22 is moved.

The console 30 is a device that accepts an operation of the X-ray CT apparatus by an operator, and that reconstructs X-ray CT image data by using counting information collected by the base 10. The console 30 includes, as shown in FIG. 1, an input interface 31, a display 32, scan control circuitry 33, preprocessing circuitry 34, projection-data storage circuitry 35, image reconstructing circuitry 36, image storage circuitry 37, and system control circuitry 38.

The input interface 31 has a mouse, a keyboard, and the like used to input various instructions and various settings by an operator of the X-ray CT apparatus, and transfers information about accepted instructions and settings to the system control circuitry 38. For example, the input interface 31 accepts a reconstruction condition at reconstructing X-ray CT image data, an image processing condition for X-ray CT image data, and the like from the operator.

The display 32 is a monitor that is referred to by the operator, and displays X-ray CT image data for the operator under control of the system control circuitry 38, and displays a graphical user interface (GUI) to accept various instructions and various settings from the operator through the input interface 31.

The scan control circuitry 33 controls collection processing of counting information by the base 10, by controlling operation of the high-voltage generator 11, the base driving circuitry 16, the data collecting circuitry 14, and the bed driver 21.

The preprocessing circuitry 34 generates projection data per energy discrimination range by performing correction processing, such as logarithmic conversion processing, offset correction, sensitivity correction, and beam hardening correction, on the counting result transmitted from the data collecting circuitry 14.

The projection-data storage circuitry 35 stores projection data generated by the preprocessing circuitry 34. That is, the projection-data storage circuitry 35 stores projection data to reconstruct X-ray CT image data.

The image reconstructing circuitry 36 generates a CT image based on a signal output by the detector 13. The image reconstructing circuitry 36 subjects the projection data stored in the projection-data storage circuitry 35 to, for example, back projection processing, thereby reconstructing X-ray CT image data. The back projection processing can be, for example, back projection processing by filtered back projection (FBP). The image reconstructing circuitry 36 can perform reconstruction processing, for example, by the successive approximation method. Furthermore, the image reconstructing circuitry 36 generates image data by performing various kinds of image processing on the X-ray CT image data. The image reconstructing circuitry 36 stores the reconstructed X-ray CT image data or image data generated by various kinds of image processing in the image storage circuitry 37.

The projection data generated from the counting result that is acquired by photon counting CT includes information about an energy of an X-ray that has been attenuated as it passes through the subject P. Therefore, the image reconstructing circuitry 36 can reconstruct, for example, X-ray CT image data of a specific energy component. Moreover, the image reconstructing circuitry 36 can reconstruct X-ray CT image data of each of multiple energy components.

Furthermore, the image reconstructing circuitry 36 can generate image data in which multiple pieces of X-ray CT image data classified by color according to the energy component are superimposed on each other, by allocating a tone according to the energy component to each pixel of X-ray CT image data of each energy component. Moreover, the image reconstructing circuitry 36 can generate, by using the K absorption edge specific to a substance, image data that enables to identify the substance. Other image data generated by the image reconstructing circuitry 36 include monochrome X-ray image data, density image data, effective-atomic-number image data, and the like.

The system control circuitry 38 performs overall control of the X-ray CT apparatus by controlling operation of the base 10, the bed 20, and the console 30. Specifically, the system control circuitry 38 controls CT scanning that is performed by the base 10, by controlling the scan control circuitry 33. Furthermore, the system control circuitry 38 controls image reconstruction processing and image generation processing that are performed by the console 30 by controlling the preprocessing circuitry 34 and the image reconstructing circuitry 36. Moreover, the system control circuitry 38 controls to display various kinds of image data that are stored in the image storage circuitry 37 on the display 32.

As above, the entire configuration of the X-ray CT apparatus according to the first embodiment has been explained. With such a configuration, the X-ray CT apparatus according to the first embodiment reconstructs X-ray CT image data by using a photon counting detector.

The SiPM 130 outputs an analog signal. This analog signal is weak, and it is preferable that an analog-to-digital converter (ADC) be arranged near the SiPM 130 in terms of avoiding mixture of noises to the analog signal. However, when the detector 13 is a surface detector, it is difficult to reserve a sufficient space to arrange an ADC near the SiPM 130.

Moreover, for the ADC, a processing performance to satisfy $10^7$ to $10^8$ (counts per second (cps)) is required at the time of converting a received analog signal to a digital signal. When such a high-speed processing performance is satisfied, ADCs have problems of a consumption current and heat. Furthermore, as ADCs cannot be fragmented as much as complementary metal oxide semiconductor (CMOS) processes, ADCs are disadvantageous for integration. As described, there are many problems in implementing a large-scale surface detector in terms of circuit scale, consumed power, processing performance, and the like.

Therefore, it is significantly advantageous to output a signal that is output from the detector in a digital signal not in an analog signal. For example, without using an ADC, a combination circuit premised on a CMOS circuit that counts an output value from the APD cell 140 directly as a digital value has been proposed. In such a combination circuit, the CMOS circuit includes a flip-flop (FF), a counter, a static random access memory (SRAM), and the like as a basic block. However, when the basic block is fragmented, a radiation can enter inside the semiconductor. In such a case, for example, there is an increased possibility of occurrence of a soft error in which the logic is reversed in the basic block such as an SRAM. When a soft error occurs in the basic block, the credibility of the photon counting processing of the detector 13 is reduced.

Furthermore, when a surface detector is structured with the SiPM 130, several thousands of pixels output data of several thousands of views per second. For the data, correction processing dependent on a detecting device is necessary, and a load of the correction processing in a later stage increases as the number of X-ray detection elements increases.

With the above reasons, in the first embodiment, structuring such that the detector 13 is not affected by radiations, the accuracy in the photon counting processing is improved. For example, the SiPM 130 is provided for each of the X-ray detection elements, and includes a capacitor that accumulates an electrical signal generated by each of the X-ray detection elements, and generating circuitry that has a low sensitivity to radiations, and that generates a digital signal by using an accumulation result of electrical signals by multiple capacitors and reference information that is stored in advance. In the following, the SiPM 130 according to the first embodiment is explained using FIG. 3 to FIG. 6.

Figure 3:
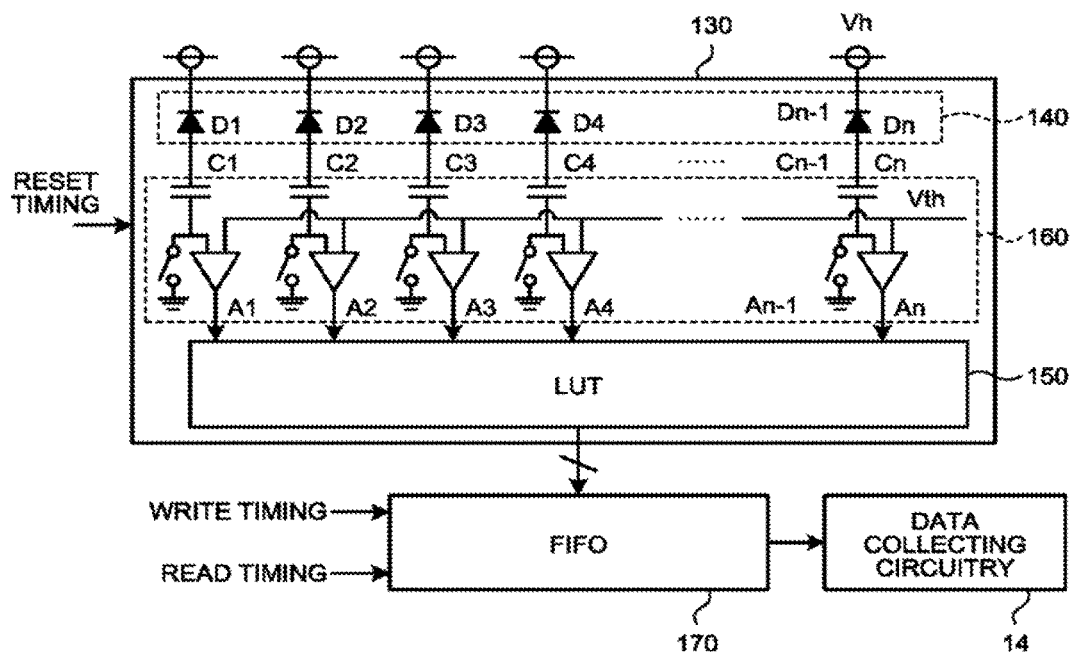
FIG. 3 shows a configuration example of a silicon photomultiplier (SiPM) according to the first embodiment.

FIG. 3 shows a configuration example of the SiPM 130 according to the first embodiment. FIG. 3 only shows the SiPM 130 corresponding to a single pixel. As shown in FIG. 3, the SiPM 130 includes the APD cell 140, a look-up table (LUT) 150, and a capacitor group 160. Vh in FIG. 3 indicates an applied voltage, and is 80 volts (V), for example. Moreover, the value of the applied voltage can be changed arbitrarily.

The APD cell 140 includes plural APDs as described above. Each APD detects one photon and outputs a signal as described above. FIG. 3 illustrates the APD cell 140 that has n units of APDs. In FIG. 3, the respective APDs are indicated as D1, D2, . . . , Dn. In the following, for example, the APD of D1 is described as APD (D1).

The capacitor group 160 has plural capacitors and plural comparators, and is provided for each of the X-ray detection element to accumulate an electrical signal generated by the X-ray detection element.

For example, the capacitor group 160 includes plural capacitors that accumulate an electrical signal generated by the respective APDs. FIG. 3 illustrates the capacitor group 160 that has n units of capacitors. In FIG. 3, the respective capacitors are indicated as C1, C2, . . . , Cn. The capacitor C1 is connected to the APD (D1), and accumulates an electrical signal that is output from the APD (D1). Furthermore, the capacitor C2 is connected to the APD (D2), and accumulates an electrical signal that is output from the APD (D2). Similarly, the capacitor Cn is connected to the APD (Dn), and accumulates an electrical signal that is output from the APD (Dn). That is, the respective capacitors accumulate electrical signals output from the corresponding APDs.

Furthermore, in the capacitor group 160, a comparator is connected to each of the capacitors. FIG. 3 illustrate the capacitor group 160 that has n units of comparators. In FIG. 3, the respective comparators are described as A1, A2, . . . , An. The comparator A1 is connected to the capacitor C1, and compares the electrical signal accumulated in the capacitor C1 with a comparison potential Vth. Moreover, the comparator A2 is connected to the capacitor C2, and compares the electrical signal accumulated in the capacitor C2 with the comparison potential Vth. Similarly, the comparator An is connected to the capacitor Cn, and compares the electrical signal accumulated in the capacitor Cn with the comparison potential Vth.

Figure 4:
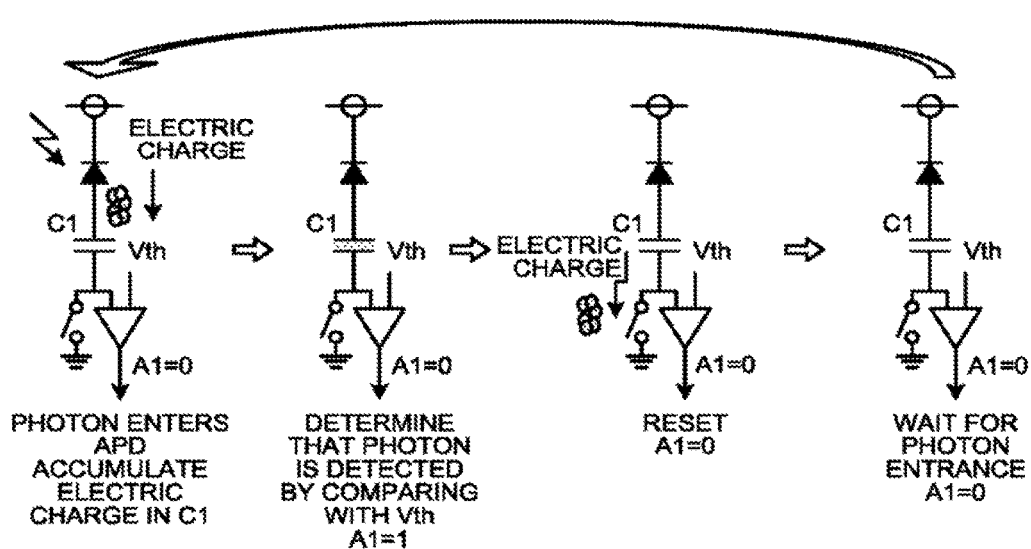
FIG. 4 is a diagram for explaining processing operation of a capacitor group according to the first embodiment.

FIG. 4 is a diagram for explaining a processing operation of the capacitor group 160 according to the first embodiment. In FIG. 4, processing operation at the time of accumulation of an electrical signal by using the capacitor C1 out of the capacitors included in the capacitor group 160 is explained, but processing operation at the time of accumulation of an electrical signal by other capacitors is also the same. As shown in a right middle drawing in FIG. 4, the capacitor C1 resets the accumulated electrical signal when a switch is closed accepting an input of a reset signal. Subsequently, as shown in a right end drawing in FIG. 4, the switch is released and the capacitor C1 turns into a standby state to wait for entrance of a photon.

Subsequently, photons randomly enter pixels in a period in which the scintillator emits light. When a photon enters each cell in each pixel, the APD makes avalanche action, and an electric current flows therein, and an electric charge is accumulated in the capacitor corresponding to each of the APDs. For example, when the APD (D1) detects a photon, as shown in a left end drawing in FIG. 4, the capacitor C1 starts accumulation of an electrical signal output from the APD (D1).

The comparator A1 then detects the accumulated electrical signal by sensing up, as shown in a left middle drawing in FIG. 4, and compares with the comparison potential Vth. When determining that the accumulated electrical signal is equal to or higher than Vth, the comparator A1 outputs 1 as an output value to the LUT 150 as an accumulation result. On the other hand, when determining that the accumulated electrical signal is lower than Vth, the comparator A1 outputs 0 as an output value to the LUT 150 as an accumulation result. Each comparator repeats processing of detecting an electrical signal accumulated in a corresponding capacitor by sensing up, and of comparing the accumulated electrical signal with the comparison potential Vth until a reset signal is input.

Explanation returns to FIG. 3. The LUT 150 is provided for each of the X-ray detection elements. For example, as shown in FIG. 3, the LUT 150 is connected to the respective comparators in one pixel. In the example shown in FIG. 3, the LUT 150 is connected to the comparator A1, the comparator A2, . . . , the comparator An in the SiPM 130.

Moreover, the LUT 150 is radiation tolerant. In other words, the LUT 150 has low sensitivity to radiation. In the first embodiment, it is explained such that the LUT 150 is configured with a mask read-only memory (ROM) or a magnetic memory.

Furthermore, the LUT 150 stores reference information in advance. The reference information herein is information in which an output value from each comparator and a value in a binary number corresponding to the output value from all the comparators are associated.

Figure 5:
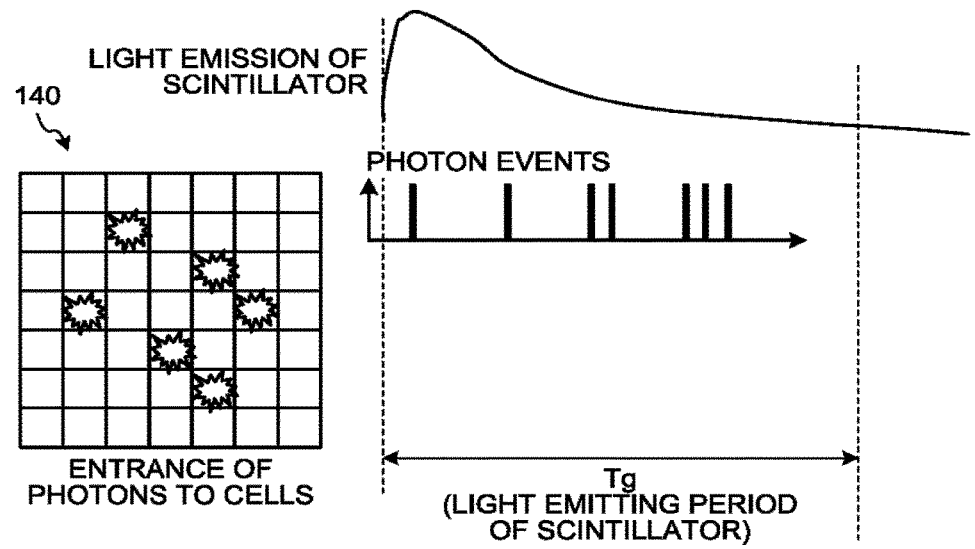
FIG. 5 is a diagram for explaining processing operation of an LUT according to the first embodiment.
Figure 6:
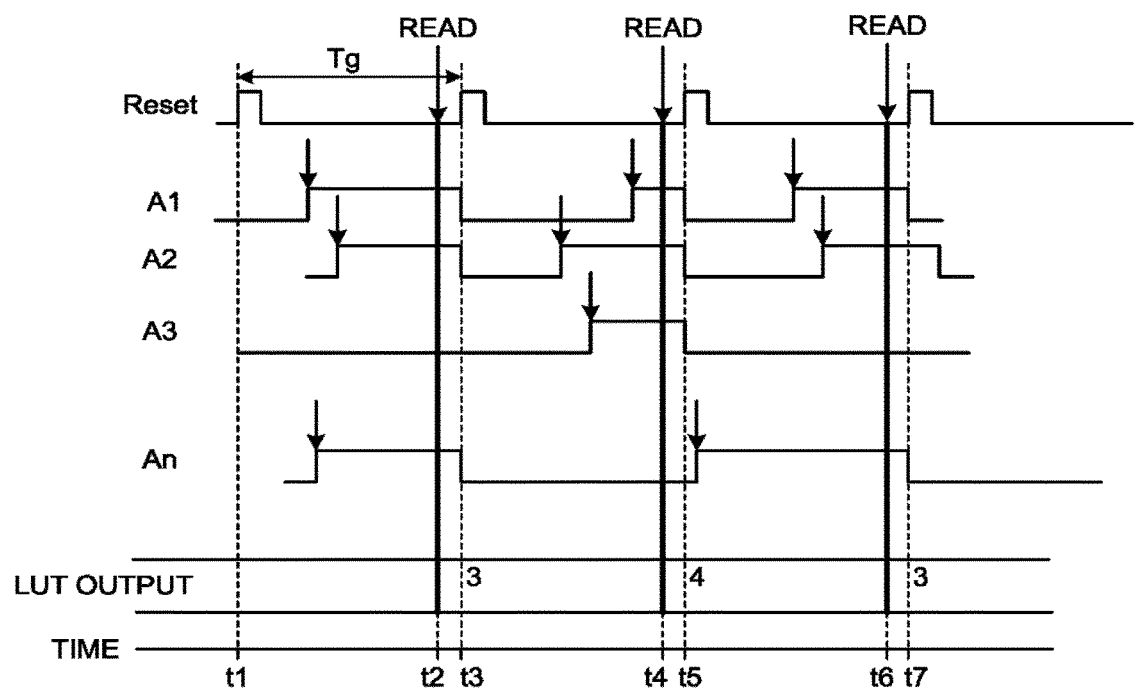
FIG. 6 is a diagram for explaining processing operation of the LUT according to the first embodiment.

The LUT 150 generates an output signal according to an accumulation result of an electrical signal generated by each of the X-ray detection elements in each predetermined period by using the reference information. For example, the LUT 150 generates a digital signal by using the accumulation result of an electrical signal in the capacitors and the reference information that is stored in advance. The LUT 150 is also referred to as generating circuitry. Subsequently, processing operation of the LUT 150 is explained using FIG. 5 and FIG. 6. FIG. 5 and FIG. 6 are diagrams for explaining processing operation of the LUT 150 according to the first embodiment.

As shown in a drawing on the right in FIG. 5, during a light emitting period of the scintillator, a gating time (Tg) that is adjusted to a period in which light is not emitted even if an X-ray enters (dead time of the scintillator) is set. This gating time corresponds to time from when a reset signal is input until when a next reset signal is input. The LUT 150 generates an output signal according to an accumulation result of electrical signals of photons detected by the APD during this gating time, in each predetermined period by using the reference information. The LUT 150 outputs a linear digital signal for the accumulation result by using the reference information.

For example, a drawing on the left in FIG. 5 shows a case in which photons are detected by six APDs during the gating time. In the case of the example shown in the drawing on the left in FIG. 5, the LUT 150 accepts an output value 1 from the six comparators, and accepts an output value 0 from the other comparators. When the reference information is information associated with a value in a binary number that indicates the number of the output value 1, the LUT 150 generates an output signal indicating the number that signifies the output value 1. More specifically, the LUT 150 generates an output signal "110" that indicates 6 in a binary number. As described, the LUT 150 accepts input of an input value from multiple APDs, and generates a digital signal corresponding to the total value of the input values based on the reference information.

FIG. 6 shows timing of processing by the LUT 150. As shown in FIG. 6, a reset signals are input at time t1, time t3, time t5, and time t7. These reset signals are input at regular intervals. Moreover, time from when a reset signal is input until when a next reset signal is input is the gating time Tg. In other words, a time when a reset signal is input synchronizes with Tg.

Furthermore, in the example shown in FIG. 6, the LUT 150 accepts the output value 1 that is output from three units of comparators, the comparator A1, the comparator An, and the comparator A2 in a period from time t1 to time t3. The LUT 150 accepts input of a read signal right before reset, and generates an output signal, and outputs the generated output signal to a first-in first-out (FIFO) 170. For example, the LUT 150 accepts input of a read signal at time t2, and generates an output signal "11" that indicates 3 in a binary number.

Moreover, in the example shown in FIG. 6, the LUT 150 accepts input of the output value 1 that is output from three units of comparators, the comparator A2, the comparator A3, and the comparator A1, and one comparator not shown in a period from time t3 to time t5. The LUT 150 then accepts input of a read signal at time t4, and generates an output signal "100" that indicates 4 in a binary number.

Similarly, in the example shown in FIG. 6, the LUT 150 accepts the output value 1 that is output from three comparators, the comparator An, the comparator A1, and the comparator A2 in a period from time t5 to time t7. The LUT 150 then accepts input of a read signal at time t6, and generates an output signal "11" that indicates 3 in a binary number.

Explanation returns to FIG. 3. The LUT 150 outputs a generated output signal to the FIFO 170 that is configured with, for example, a magnetic memory. The FIFO 170 accepts input of output signals that are output from the respective LUTs 150 included in the detector 13 in parallel, and outputs to the data collecting circuitry 14 in series.

The data collecting circuitry 14 collects an output signal from the respective X-ray detection elements. For example, the data collecting circuitry 14 discriminates the output signal per energy bin, and adds the discriminated output signals to create a histogram. Thus, the image reconstructing circuitry 36 reconstruct an image by using the output signals collected by the data collecting circuitry 14.

As described above, in the first embodiment, the LUT 150 having radiation tolerance generates an output signal according to an accumulation result of an electrical signal that is generated by an APD that has detected a photon in each predetermined period, by using the reference information. That is, in the first embodiment, an output value from the APD cell 140 is converted into a digital signal to be output, without using an ADC. This enables to reduce mixture of noises to an output value from the APD cell 140.

Furthermore, in the first embodiment, an output value from the APD cell 140 is converted into a digital signal without using an ADC. Thus, the detector 13 can be formed as a surface detector without making the detector 13 in a large scale in terms of circuit scale, consumed power, processing performance, and the like.

Moreover, by configuring the LUT 150 with a mask ROM that is not affected by radiation, even when a radiation enters the semiconductor, occurrence of a soft error can be prevented. As a result, reduction of the credibility of photon counting processing by the detector 13 can be prevented. As described, according to the first embodiment, the accuracy of the photon counting processing can be improved.

Modification of First Embodiment

Figure 7A:
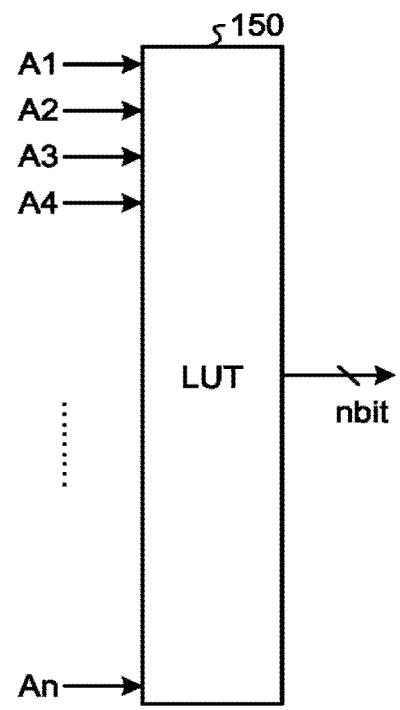
FIG. 7A is a diagram for explaining a modification of the first embodiment.
Figure 7B:
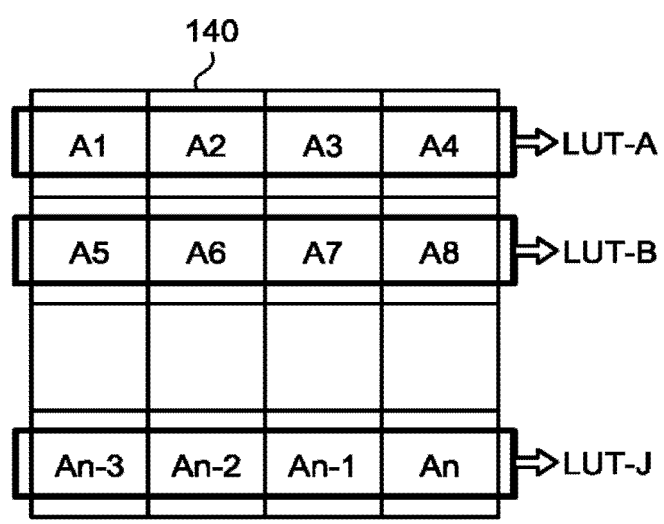
FIG. 7B is a diagram for explaining a modification of the first embodiment.
Figure 7C:
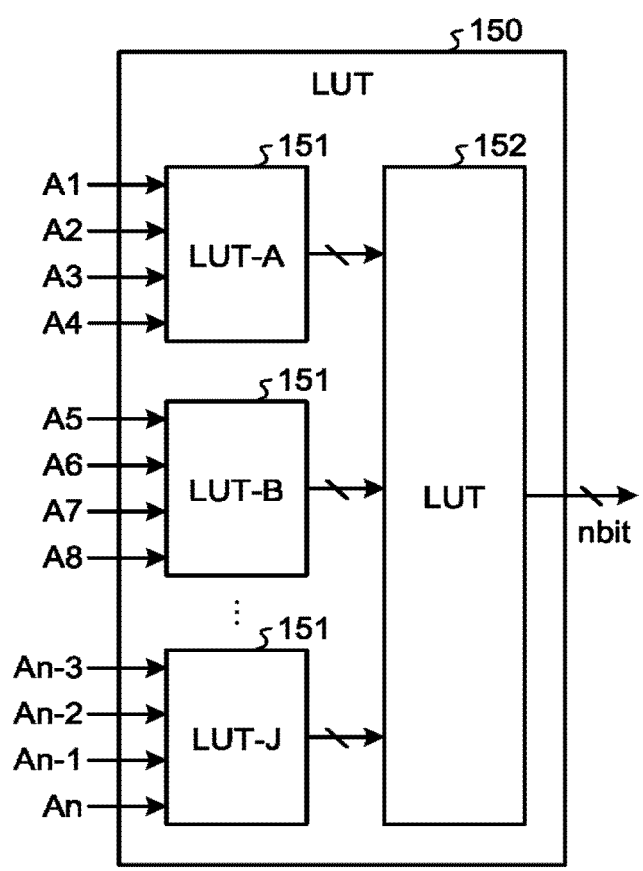
FIG. 7C is a diagram for explaining a modification of the first embodiment.

The first embodiment is not limited to the embodiment described above. In the following, a modification of the first embodiment is explained using FIG. 7A to FIG. 7C. FIG. 7A to FIG. 7C are diagrams for explaining the modification of the first embodiment.

In the above embodiment, explanation has been given assuming that the number of the APDs 141 constituting one pixel is several hundreds to several thousands. For example, when the number of the APDs 141 constituting one pixel is n, the LUT 150 accepts input of an output value that is output from the comparator corresponding to the each corresponding APDs 141 as shown in FIG. 7A. The comparator A1 shown in FIG. 7A is a comparator corresponding to the APD (D1), and the comparator A2 is a comparator corresponding to the APD (D2). Furthermore, the comparator A3 shown in FIG. 7A is a comparator corresponding to the APD (D3), the comparator A4 is a comparator corresponding to the APD (D4), and the comparator An is a comparator corresponding to the APD (Dn).

However, when the number of the APDs 141 constituting one pixel is large, wirings between the capacitor group 160 and the LUT 150 become complicated. Therefore, as shown in FIG. 7B, for example, the APDs 141 can be grouped in a direction of rows, and are caused to input an output signal to the respective LUTs in a group unit. In other words, the LUT is provided for each predetermined number of capacitors, and generates a digital signal by using an accumulation result of each predetermined number of capacitors and the reference information.

More specifically, in FIG. 7B, the comparator A1, the comparator A2, the comparator A3, and the comparator A4 corresponding to the APD 141 on the first row are grouped, and caused to input an output signal to an LUT-A. Moreover, the comparator A5, the comparator A6, the comparator A7, and the comparator A8 corresponding to the APD 141 on the second row are grouped, and caused to input an output signal to an LUT-B. Similarly, a comparator An-3, a comparator An-2, a comparator An-1, and the comparator An corresponding to the APD 141 on the n-th row are grouped, and caused to input an output signal to an LUT-J.

Each of the LUTs generates a digital signal by using an accumulation result per predetermined number of capacitors and the reference information. In such a case, each of the LUTs output the generated digital signal to the FIFO 170.

Moreover, as shown in FIG. 7C, the LUT 150 can include a first LUT 151 and a second LUT 152. In the example shown in FIG. 7C, the LUT 150 has the LUT-A, the LUT-B, . . . , and the LUT-J as the first LUT 151. The first LUT 151 is provided per predetermined number of capacitors, and generates a first digital signal by using an accumulation result per predetermined number of capacitors and first reference information. More specifically, the first LUT 151 shown in FIG. 7C groups the APDs 141 in a direction of rows similarly to the example shown in FIG. 7B, and accepts input of an output signal that is output per grouped unit.

The second LUT 152 generates a second digital signal by using the first digital signal generated by the first LUT 151 and second reference information, and handles the generated second digital signal as a digital signal. More specifically, as shown in FIG. 7C, the second LUT 152 generates the second digital signal by using the first digital signal that is generated by the LUT-A, the LUT-B, . . . , and the LUT-J, which are the first LUT 151, and the second reference information. The second LUT 152 outputs the generated second digital signal to the FIFO 170.

Although a case of grouping the APDs 141 in a direction of rows has been explained in the modification of the first embodiment described above, the embodiment is not limited thereto. For example, the APDs 141 can be grouped in a direction of columns.

Second Embodiment

In the first embodiment, it has been explained that the LUT 150 is configured with a mask ROM, and a linear output signal is output with respect to an accumulation result by using the reference information. The detector 13 can be in a failed state in which the APDs included in one pixel or the one pixel itself detects a photon all the time even when there is no incident X-rays. In such a case, it is desirable that an output signal from the APD in a failed state or the pixel in a failed state be corrected.

Therefore, in the second embodiment, a case in which reference information is information in which a non-linear value is associated with number of an output value 1 in a binary number is explained. That is, in the second embodiment, the LUT outputs a non-linear digital signal with respect to an accumulation result by using the reference information.

Figure 8:
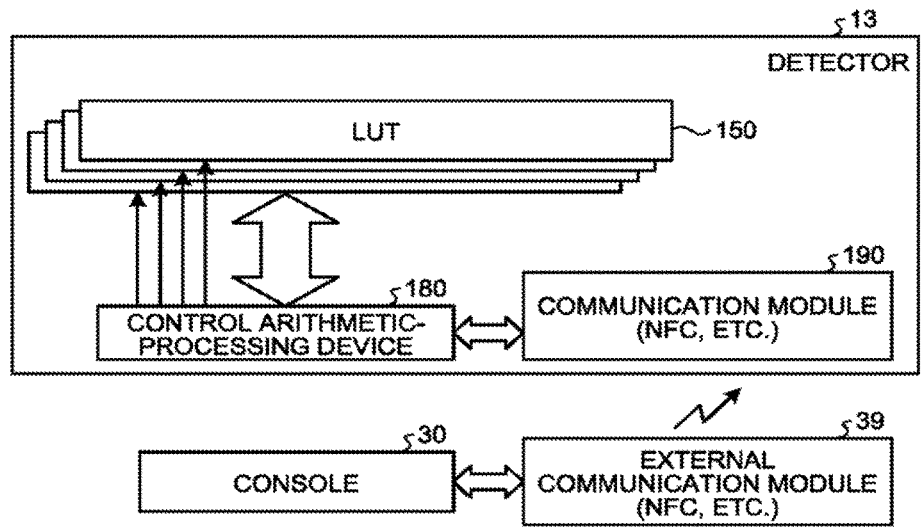
FIG. 8 shows a configuration example of a detector according to a second embodiment.

The entire configuration of an X-ray CT apparatus according to the second embodiment is the same as the configuration example shown in FIG. 1, except a point that a part of configuration inside the detector 13 differs. Therefore, explanation of the same configuration as that in FIG. 1 is omitted. FIG. 8 shows a configuration example of the detector 13 according to the second embodiment.

In the example shown in FIG. 8, the detector 13 is illustrated in a simplified manner. For example, in FIG. 8, only the LUT 150 in the SiPM 130 included in the detector 13 is illustrated. In the second embodiment, the LUT 150 is configured with, for example, a magnetic memory. In the LUT 150 configured with a magnetic memory, rewrite of reference information is possible. Furthermore, the detector 13 includes, as shown in FIG. 8, a control arithmetic-processing device 180 and a communication module 190.

Moreover, outside the detector 13, an external communication module 39 that functions under control of the console 30 is provided. Although a case of providing the external communication module 39 outside the console 30 is shown in the example shown in FIG. 8, the external communication module 39 can be provided inside the console 30.

The communication module 190 and the external communication module 39 can communicate with each other by using a near field communication (NFC) or Bluetooth (registered trademark). For example, the external communication module 39 transmits reference information to the communication module 190 under control of the console 30.

The console 30 detects a failure of each pixel or the APD 141 in advance, for example, and generates reference information such that an output signal from the failed pixel or the failed APD is not reflected thereto. More specifically, for an APD, an output value of which is always 1 in a state in which no X-rays are entering, or for a pixel for which an output value from all of the APDs is always 1 in a state in which no X-rays are entering, reference information is generated such that the output signal is excluded from a count value. As described, the reference information indicates a predetermined correction value for an accumulation result.

The communication module 190 then transfers the reference information received from the external communication module 39 to the control arithmetic-processing device 180. The control arithmetic-processing device 180 sets the received reference information in each of the LUTs 150. That is, the reference information can be set by an access from an external device.

The LUT 150 according to the second embodiment generates an output signal in which an output value from a failed APD or a failed pixel is corrected by using the reference information. In other words, the LUT 150 according to the second embodiment can perform correction processing as preprocessing, by using the reference information. The correction processing can be performed also in a later stage. However, when the correction processing is performed by software in a later stage, floating-point arithmetic is necessary for each of several thousands of pixels. Therefore, the correction processing in a later stage requires time. On the other hand, the LUT 150 according to the second embodiment can omit the correction processing in a later stage for each of several thousands of pixels, and therefore, can shorten time required for image reconstruction. As a result, the X-ray CT apparatus according to the second embodiment can reduce a processing load and improve the throughput.

Moreover, the LUT 150 can implement correction processing other than that of simple photon counting, by positively using this reference information. For example, a dark current with which an APD makes can occur at a certain probability even when no X-rays are entering. Therefore, a count value corresponding to the dark current is estimated in advance, and reference information in which the count value corresponding to the dark current is corrected is set in the LUT 150. The LUT 150 can output an output signal in which the count number corresponding to the dark current is corrected. Furthermore, for example, when a dummy count value appears statistically, reference information in which this dummy count value is excluded can be set in the LUT 150.

Modification of Second Embodiment

Although a case in which reference information indicates a predetermined correction value with respect to an accumulation result has been explained in the second embodiment, the embodiment is not limited thereto. For example, the reference information can indicate an energy band according to an accumulation result. More specifically, the count value is further replaced with an energy bin. For example, the reference information is set such that when a value of a count value α is α1<α≤α2, it is discriminated to an energy E1; when α2<α≤α3, it is discriminated to an energy E2; when α3<α≤α4, it is discriminated to an energy E3; and when α4<α≤α5, it is discriminated to an energy E4. Thus, the LUT 150 is enabled to generate an output signal that indicates a count value per energy band by using the reference information. That is, as the X-ray CT apparatus can discriminate energies in the detector 13, the processing load in a later stage can be reduced.

Moreover, although a case in which reference information is set in the LUT 150 by wireless communication such as an NFC and Bluetooth (registered trademark) has been explained in the second embodiment, the embodiment is not limited thereto. For example, the LUT 150 can be configured to have a dual port interface. In such a case, the LUT 150 accepts a specification of an address and data corresponding to the address from an external unit, to set reference information.

Furthermore, when an address and data are specified from an external unit to the LUT 150 having a dual port interface to set reference information, a control signal, such as CS (clear to send), WR, and RD, can be of either parallel or serial. If the control signal is of serial, there are many advantages, such as decreased signal lines.

Moreover, although a case in which reference information is set as an initial value has been explained in the second embodiment and the modification of the second embodiment described above, the embodiment is not limited thereto. For example, the second embodiment and the modification of the second embodiment described above can be applied similarly when the reference information set as the initial value is rewritten.

Although a case in which the LUT 150 is configured with a magnetic memory has been explained in the second embodiment and the modification of the second embodiment, the embodiment is not limited thereto. For example, the second embodiment and the modification of the second embodiment described above can be applied similarly to the LUT 150 according to the first embodiment that is configured with a mask ROM. Note that in the LUT 150 according to the first embodiment that is configured with a mask ROM, reference information cannot be updated.

Third Embodiment

In the second embodiment, a case of setting reference information of the LUT in advance by an external device has been explained. The property of the detector 13 changes according to the temperature. Moreover, the dark current is temperature-dependent. Therefore, the reference information of the LUT can be dynamically rewritten according to changes in temperature in the detector 13. Accordingly, in the third embodiment, ca case in which the temperature in the detector 13 is measured by a temperature sensor, and reference information of the LUT is rewritten in real time according to changes in the temperature is explained.

Figure 9:
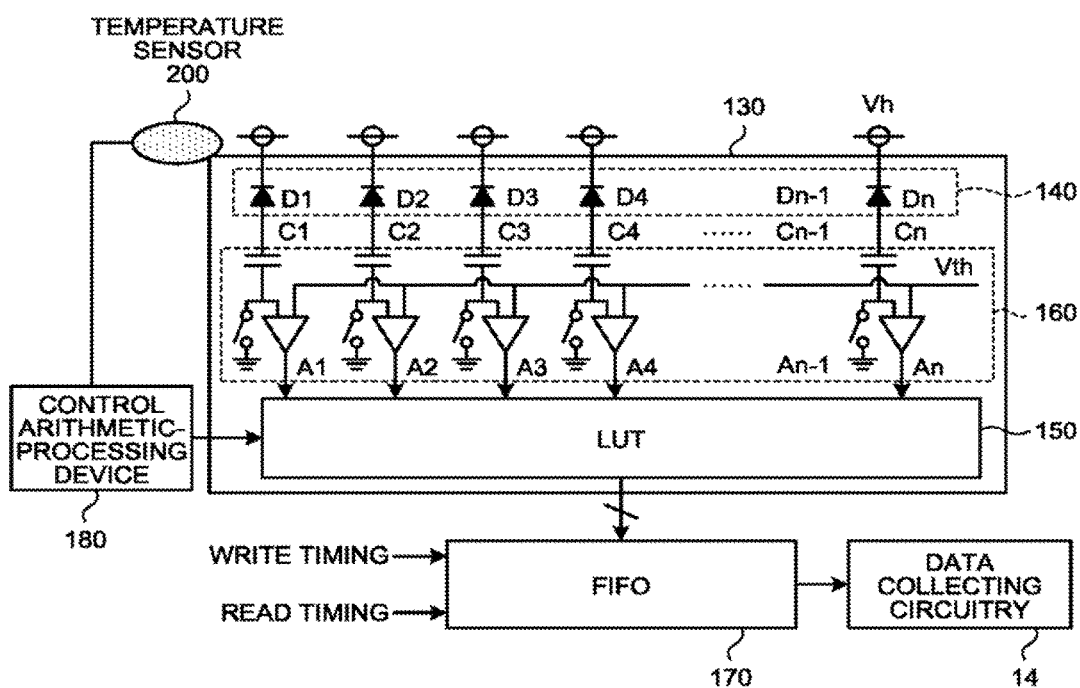
FIG. 9 shows a configuration example of a SiPM according to a third embodiment.

The entire configuration of the X-ray CT apparatus according to the third embodiment is the same as the configuration example shown in FIG. 1, except a point that a part inside the detector 13 differs. Therefore, explanation of the configuration same as that in FIG. 1 is omitted. FIG. 9 shows a configuration example of the SiPM 130 according to the third embodiment. The APD cell 140 and the capacitor group 160 have the same functions as the APD cell 140 and the capacitor group 160 explained in FIG. 3.

As shown in FIG. 9, a temperature sensor 200 is arranged near the SiPM 130. In the example shown in FIG. 9, it is explained such that the temperature sensor 200 is arranged near each of the SiPMs 130, only one unit of the temperature sensor 200 can be provided in the detector 13, or one unit thereof can be provided for each several units of SiPMs 130.

The LUT 150 according to the third embodiment stores more than one piece of reference information. For example, the LUT 150 according to the third embodiment stores multiple pieces of reference information according to temperature. In the following, a case in which the LUT 150 stores reference information A, reference information B, reference information C, and reference information D is explained.

When a temperature measured by the temperature sensor 200 is T, the reference information A is reference information in which a dark current that is assumed to occur when T<T1 is corrected. Moreover, the reference information B is reference information in which a dark current that is assumed to occur when T1≤T<T2 is corrected. The reference information C is reference information in which a dark current that is assumed to occur when T2≤T<T3 is corrected. Furthermore, the reference information D is reference information in which a dark current that is assumed when T3≤T is corrected. Note that temperature T1<temperature T2<temperature T3.

The temperature sensor 200 measures a temperature, and outputs the measured temperature to the control arithmetic-processing device 180. The control arithmetic-processing device 180 selects one out of the multiple pieces of reference information according to the temperature measured by the temperature sensor 200. For example, the control arithmetic-processing device 180 compares a temperature T with temperatures T1, T2, and T3, and determines to which temperature range out of temperature ranges of temperatures T1 to T3, temperature T measured by the temperature sensor 200 is approximated. The control arithmetic-processing device 180 selects appropriate one of the reference information based on a result of determination, to set in the LUT 150. Thus, the LUT 150 generates an output signal by using the selected reference information. As one example, the control arithmetic-processing device 180 selects the reference information C when temperature T is T2≤T<T3, for example, and set it in the LUT 150. In this case, the LUT 150 generates an output signal by using the reference information C.

The control arithmetic-processing device 180 switches reference information during a view interval, a slice interval, or a reset period of the SiPM 130, and is not switch during image collection.

Although it has been explained that the LUT 150 stores multiple pieces of reference information in the third embodiment, the embodiment is not limited thereto. For example, the control arithmetic-processing device 180 can generate reference information in real time based on a temperature measured by the temperature sensor 200, and set the generated reference information in the LUT 150. In other words, the control arithmetic-processing device 180 rewrites reference information in real time according to a temperature measured by the temperature sensor 200.

Moreover, although the temperature in the detector 13 and a count corresponding to a dark current have been explained in the third embodiment, the embodiment is not limited thereto. For example, it can be configured to switch reference information by a similar system even for an external factor other than the temperature.

Other Embodiments

The embodiment is not limited to the embodiments described above.

For example, although it has been explained that one unit of capacitor is provided to each of the APDs 141 in the capacitor group 160 in the embodiment explained above, the embodiment is not limited thereto. For example, the capacitor group 160 can be arranged such that more than one capacitor is provided to each of the APDs 141, and that an electrical signal is accumulated while switching the capacitors in a predetermined period. In other words, multiple units of capacitors are provided to each of the APDs 141, and are switched in a predetermined period to accumulate an electrical signal. FIG. 10 A to FIG. 10D is diagrams for explaining the capacitor group 160 according to another embodiment.

Figure 10A:
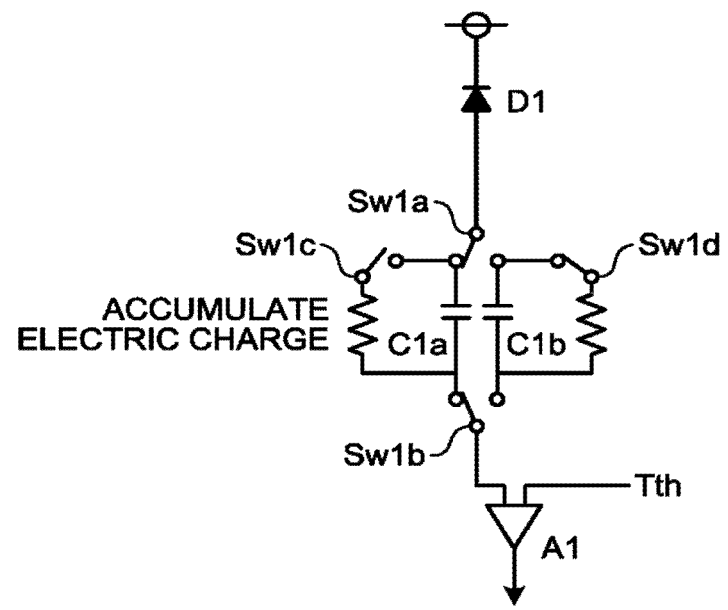
FIG. 10A is a diagram for explaining a capacitor group according to another embodiment.

FIG. 10A shows a configuration example of a capacitor that is included in the capacitor group 160 according to the other embodiment. In FIG. 10A, only a capacitor C1$a$ and a capacitor C1$b$ out of capacitors included in the capacitor group 160 according to the other embodiment are illustrated to give explanation. As shown in FIG. 10A, the capacitor C1$a$ and the capacitor C1$b$ are provided for the APD (D1). Either of the capacitor C1$a$ and the capacitor C1$b$ is selectively connected to the APD (D1). Furthermore, the comparator A1 is provided for the capacitor C1$a$ and the capacitor C1$b$. The capacitor C1$a$ and the capacitor C1$b$ is selectively connected to the comparator A1.

Figure 10B:
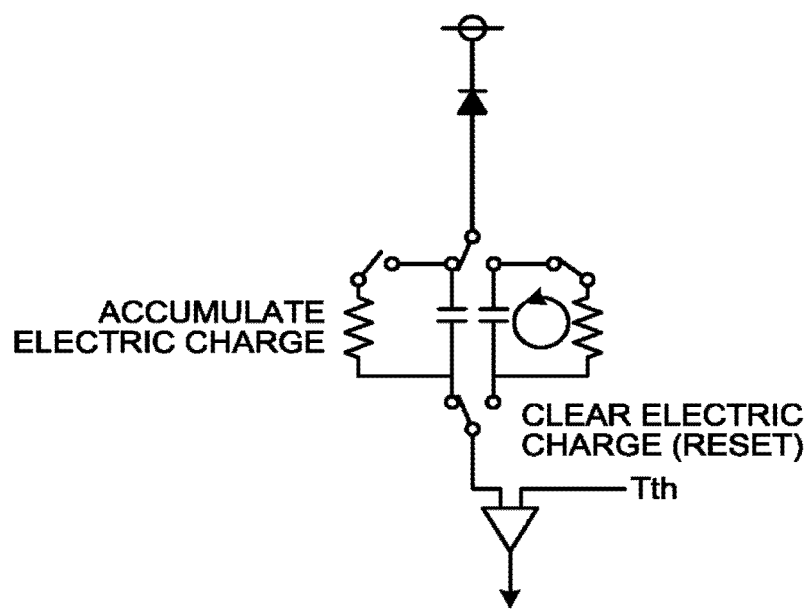
FIG. 10B is a diagram for explaining a capacitor group according to another embodiment.

For example, as shown in FIG. 10B, accepting input of a selection signal, a switch Sw1$a$ and a switch Sw1$b$ are connected to the capacitor C1$a$, and thus, the capacitor C1$a$ is connected to the APD (D1). When a switch Sw1$c$ is released accepting input of a selection signal, the capacitor C1$a$ accumulates an electrical signal output from the APD (D1). The comparator A1 then detects the electrical signal accumulated in the capacitor C1$a$ by sensing up, and compares it with the comparison potential Vth. When determining that the accumulated electrical signal is equal to or higher than Vth, the comparator A1 outputs 1 as an output value to the LUT 150 as an accumulation result. In the following, when an accumulation result of an electrical signal accumulated in the capacitor C1$a$ is output, it is described as output value A1-1. In the example shown in FIG. 10B, Sw1$d$ is closed accepting input of a selection signal, and the electrical signal accumulated in the capacitor C1$b$ is reset.

Figure 10C:
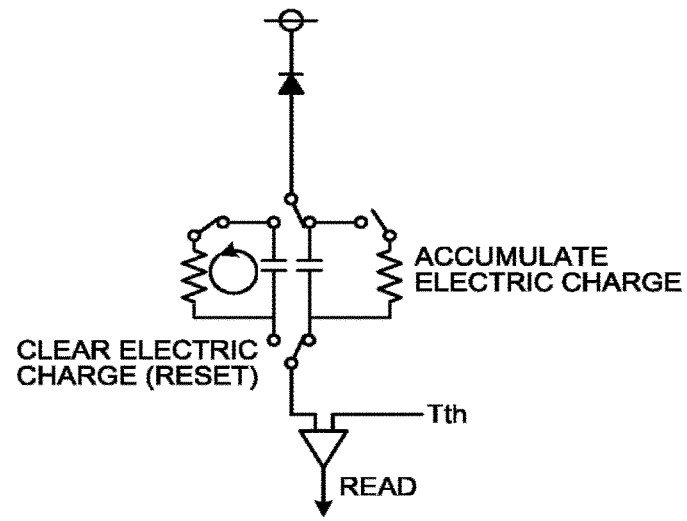
FIG. 10C is a diagram for explaining a capacitor group according to another embodiment.
Figure 10D:
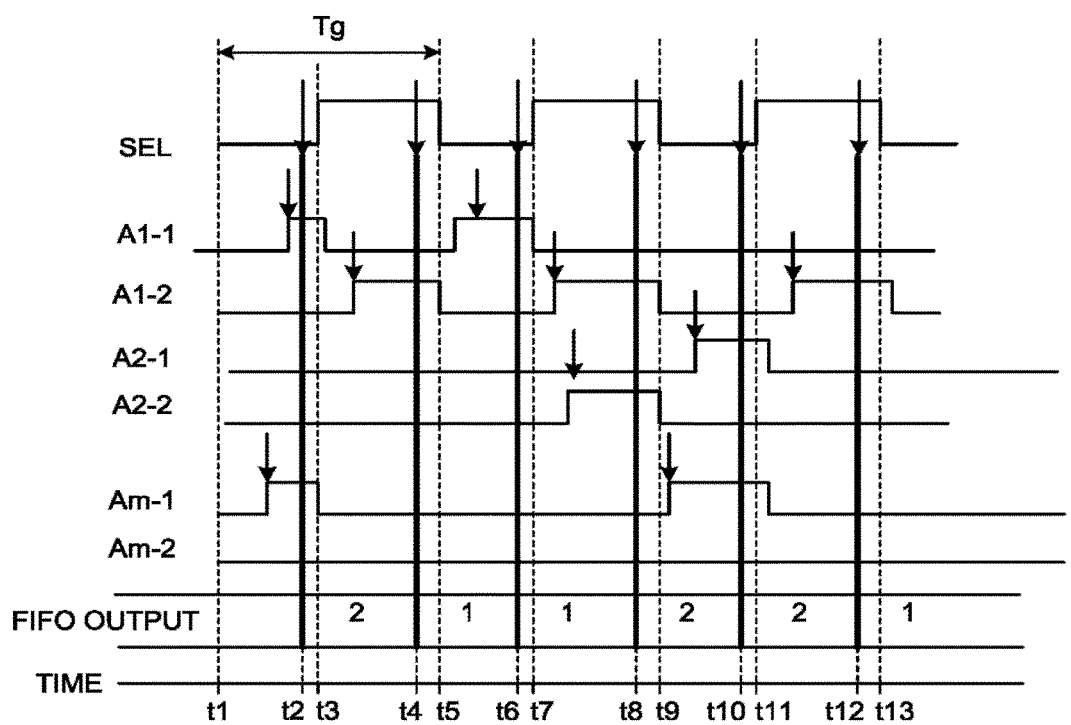
FIG. 10D is a diagram for explaining a capacitor group according to another embodiment.

Moreover, for example, as shown in FIG. 10C, accepting input of a selection signal, the switch Sw1$a$ and the switch Sw1$b$ are connected to the capacitor C1$b$, and thus, the capacitor C1$b$ is connected to the APD (D1). When the switch Sw1$d$ is released, accepting input of a selection signal, the capacitor C1$b$ accumulates an electrical signal output from the APD (D1). The comparator A1 then detects the electrical signal accumulated in the capacitor C1$b$ by sensing up, and compares it with the comparison potential Vth. When determining that the accumulated electrical signal is equal to or higher than Vth, the comparator A1 outputs 1 as an output value to the LUT 150 as an accumulation result. In the following, when an accumulation result of an electrical signal accumulated in the capacitor C1$b$ is output, it is described as output value A1-2. In the example shown in FIG. 10C, Sw1$c$ is closed accepting input of a selection signal, and the electrical signal accumulated in the capacitor C1$a$ is reset.

FIG. 10D shows timing of processing by the LUT 150 when multiple units of capacitors are provided for each of the APDs. In the example shown in FIG. 10D, time t1 to time t5, time t5 to time t9, and time t9 to time t13 are the gating times. Moreover, as shown in FIG. 10D, the capacitor group 160 accepts input of selection signals at time t3, time t5, time t7, time t9, time t11, and time t13.

Furthermore, in the example shown in FIG. 10D, during a period from time t1 to time t5, after the LUT 150 accepts input of an output value 1 from two comparators of the comparator A1-1 and the comparator Am-1 at time t2, the LUT 150 generates an output signal based on the output value output from the comparator A1-1 and the comparator Am-1, and outputs the generated output signal to the FIFO 170. Furthermore, the input of the LUT 150 is switched to A1-2, . . . , Am-2 after accepting input of the selection signal at time t3, and at the same time, the capacitor of the comparators A1-1, . . . , Am-1 is reset. Thereafter, after accepting input of the output value 1 output from the comparator A1-2 connected to the LUT 150 at t4, the LUT 150 generates an output signal based on the output value output from the comparator A1-2, and outputs the generated output signal to the FIFO 170.

Moreover, in the example shown in FIG. 10D, during a period from time t5 to time t9, after the LUT 150 accepts input of an output value 1 from the comparator A1-1 at time t6, the LUT 150 generates an output signal based on the output value output from the comparator A1-1, and outputs the generated output signal to the FIFO 170. Furthermore, the input of the LUT 150 is switched to A1-2, . . . , Am-2 after accepting input of the selection signal at time t7, and at the same time, the capacitor of the comparators A1-1, . . . , Am-1 is reset. Thereafter, after accepting input of the output value 1 output from two comparators of the comparator A1-2 and a comparator A2-2 connected to the LUT 150 at t8, the LUT 150 generates an output signal based on the output value output from the comparator A1-2 and the comparator A2-2, and outputs the generated output signal to the FIFO 170.

Similarly, in the example shown in FIG. 10D, during a period from time t9 to time t13, after the LUT 150 accepts input of an output value 1 from two comparators of the comparator Am-1 and the comparator A2-1 at time t10, the LUT 150 generates an output signal based on the output value output from the comparator Am-1 and the comparator A2-1, and outputs the generated output signal to the FIFO 170. Furthermore, the input of the LUT 150 is switched to A1-2, . . . , Am-2 after accepting input of the selection signal at time t11, and at the same time, the capacitor of the comparators A1-1, . . . , Am-1 is reset. Thereafter, after accepting input of the output value 1 output from the comparator A1-2 connected to the LUT 150 at t12, the LUT 150 generates an output signal based on the output value output from the comparator A1-2, and outputs the generated output signal to the FIFO 170.

As the above embodiment, by arranging more than one capacitor in one cell, and by sequentially switching connection with a sense amplifier, photon counting can be performed frequently. Thus, the number of counts countable at the time of high dose can be increased, and pileup can be suppressed.

Figure 11:
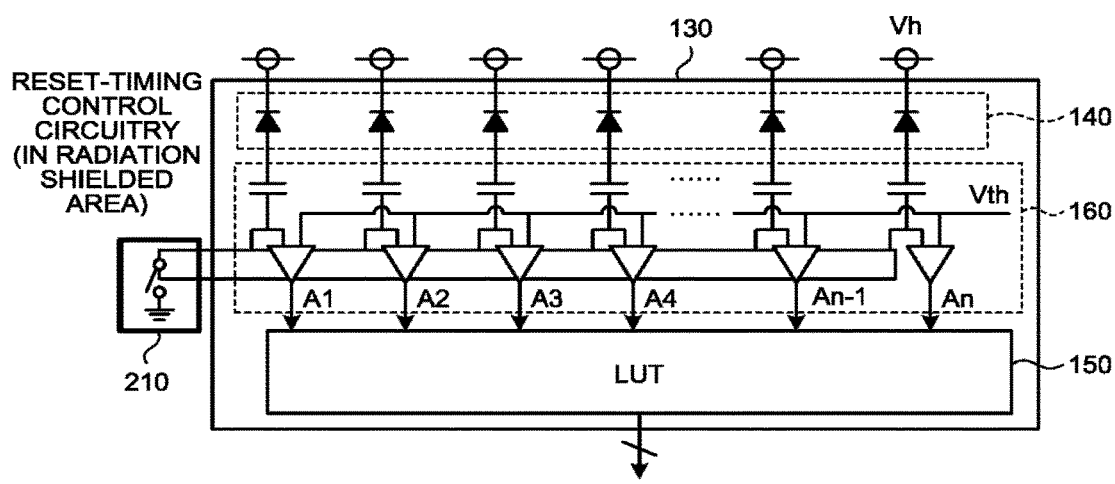
FIG. 11 shows a configuration example of a SiPM according to another embodiment.

Moreover, in the above embodiment, the capacitor group 160 has been explained to reset an electrical signal accumulated in the capacitor by controlling individual switches when a reset signal is accepted. As the reset switch is generally structured with a transistor, a soft error can occur. In such a case, the reset signal can be switched from off to on. For this reason, an embodiment of preventing a soft error in the reset switch is explained. FIG. 11 shows a configuration example of the SiPM 130 according to another embodiment.

As shown in FIG. 11, outside the SiPM 130, reset-timing control circuitry 210 is provided. The reset-timing control circuitry 210 is provided within a radiation shielded area. The reset-timing control circuitry 210 deletes the accumulated electrical signal after predetermined period. The predetermined period is set based on a light emitting period of the scintillator arranged in an indirect conversion X-ray detection element. For example, the predetermined period is longer than time in which the light emission of the scintillator decreases to a half. The reset-timing control circuitry 210 outputs a reset signal to delete an electrical signal accumulated in each capacitor at a predetermined time, to each of the capacitors. Each of the reset switches to delete the electrical signal accumulated in the respective capacitors is controlled by the reset signal output from the reset-timing control circuitry 210.

For example, as shown in FIG. 11, in the capacitor group 160, each the reset switches to delete an electrical signal accumulated in each of the capacitors is connected to the other reset switches in series. The capacitor group 160 deletes the accumulated electrical signal based on the reset signal output from the reset-timing control circuitry 210 in synchronization with the other reset switches. In other words, the respective reset switches delete the electrical signal accumulated in the respective capacitors based on the reset signal output from the reset-timing control circuitry 210 in synchronization with the other switches. Thus, the X-ray CT apparatus can prevent a soft error in the reset switch. Although a case in which the reset-timing control circuitry 210 is arranged in the radiation shielded area has been explained in the example shown in FIG. 11, it is not limited thereto. For example, if it is possible to configure such that reset processing is not performed unless the respective reset switches are simultaneously on, the reset-timing control circuitry 210 can be arranged outside the radiation shielded area.

Although it has been explained that the detector 13 is supported by the rotating frame 15, and rotates at high speed along a circular orbit with the subject P in center thereof in the above embodiment, the embodiment is not limited thereto. For example, the embodiment can be applied also when multiple units of photon counting detectors (PCD) are arranged in the fourth-generation arrangement. In the fourth-generation X-ray CT apparatus, a predetermined number of the photon counting detectors (PCD) are arranged sparsely at fixed positions along a predetermined circle around a subject to be scanned. Furthermore, the embodiment described above can be applied also to a hybrid X-ray CT apparatus that has the third-generation energy integration detectors arranged in a geometric form, and the fourth-generation photon counting detectors (PCD) arranged sparsely in a geometric form.

Moreover, although a case in which the detector 13 is an indirect-conversion photon counting detector has been explained in the above embodiment, the embodiment is not limited thereto. For example, the X-ray detection element of the detector 13 can be of a direct conversion type. In such a case, the X-ray detection element is configured with a cadmium telluride (CdTe) semiconductor, a cadmium zinc telluride (CdZnTe) semiconductor, or the like.

In the explanation of the above embodiments, the illustrated respective components of the respective devices are of functional concept, and are not necessarily required to be physically configured as shown in the drawings. Specifically, a specific form of distribution and integration of the respective devices are not limited to the ones shown in the drawings, and all or a part thereof can be configured to be functionally or physically distributed or integrated in arbitrary units according to various kinds of loads and usage conditions, and the like. Furthermore, as for the respective processing functions performed by the respective devices, all or an arbitrary part thereof can be implemented by a central processing unit (CPU) and a computer program that is analyzed and executed by the CPU, or can be implemented as hardware by wired logic.

Moreover, the control method explained in the above embodiments can be implemented by executing a control program prepared in advance by a computer, such as a personal computer and a workstation. The control program can be distributed through a network such as the Internet. Furthermore, the control program can be stored in a computer-readable recording medium, such as a hard disk, a flexible disk (FD), a compact-disc read-only memory (CD-ROM), a magneto optical disk (MO), and a digital versatile disc (DVD), and can be executed by being read by a computer from the recording medium.

According to at least one of the embodiments explained above, the accuracy of photon counting processing can be improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A photon counting detector, comprising:
a plurality of X-ray detection elements configured to detect an X-ray and generate an electrical signal;
a plurality of capacitors, each being connected to a different one of the plurality of X-ray detection elements without an intervening amplifier, and accumulating an electrical signal generated in the one of the plurality of X-ray detection elements, wherein no transistor is connected to each of the plurality of capacitors without an intervening circuit element; and
generating circuitry configured to store reference information, and generate a digital signal by using an accumulation result of the electrical signal in each of the plurality of capacitors and the reference information.

2. The photon counting detector according to claim 1, wherein the generating circuitry is further configured to output a linear digital signal for the accumulation result by using the reference information.

3. The photon counting detector according to claim 2, wherein the X-ray detection element includes a plurality of photoelectric converters, and
the generating circuitry is further configured to accept input of an output value from the photoelectric converters, and generate the digital signal corresponding to a total value of the input value based on the reference information.

4. The photon counting detector according to claim 1, wherein the generating circuitry is further configured to output a non-linear digital signal for the accumulation result by using the reference information.

5. The photon counting detector according to claim 4, wherein the reference information indicates a predetermined correction value for the accumulation result.

6. The photon counting detector according to claim 4, wherein the reference information indicates an energy band according to the accumulation result.

7. The photon counting detector according to claim 1, wherein the generating circuitry includes a mask read-only memory (ROM).

8. The photon counting detector according to claim 1, wherein the generating circuitry includes a magnetic memory.

9. The photon counting detector according to claim 8, wherein the reference information stored by the generating circuitry can be set by an external device.

10. The photon counting detector according to claim 9, further comprising a temperature sensor, wherein
the external device rewrites the reference information in real time according to a temperature measured by the temperature sensor.

11. The photon counting detector according to claim 10, wherein
the generating circuitry stores a plurality of pieces of reference information, and
the external device selects one of the plurality of pieces of reference information according to the temperature measured by the temperature sensor.

12. The photon counting detector according to claim 1, further comprising control circuitry configured to output each of control signals to each of the plurality of capacitors, each of the control signals being configured to control deletion of an electrical signal accumulated in each of the plurality of capacitors at a predetermined time,
wherein each of switches to delete the electrical signal accumulated in each of the plurality of capacitors is controlled by one of the control signals output from the control circuitry.

13. The photon counting detector according to claim 12, wherein the control circuitry is arranged in a radiation shielded area.

14. The photon counting detector according to claim 12, wherein
the control circuitry is further configured to delete the accumulated electrical signal after a predetermined period, and
the predetermined period is set based on a light emitting period of a scintillator of an indirect-conversion X-ray detection element.

15. The photon counting detector according to claim 14, wherein the predetermined period after which the control circuitry deletes the accumulated electrical signal is longer than a time period over which light emission of the scintillator decreases by half.

16. The photon counting detector according to claim 12, wherein each of the plurality of switches to delete the electrical signal accumulated in each of the plurality of capacitors is connected to each of second switches in series, and causes the electrical signal accumulated in each of the plurality of capacitors to be deleted in synchronization with each of the second switches, based on the control signal output from the control circuitry.

17. The photon counting detector according to claim 1, wherein each of the X-ray detection elements is an indirect-conversion X-ray detection element that includes a plurality of photoelectric converters.

18. The photon counting detector according to claim 17, wherein each of the plurality of capacitors is provided for each of the photoelectric converters, and the plurality of capacitors are switched thereamong in a predetermined period, to accumulate the electrical signal.

19. The photon counting detector according to claim 1, wherein the generating circuitry is provided for each of the predetermined number of capacitors and is configured to generate the digital signal by using an accumulation result per predetermined number of capacitors and the reference information.

20. The photon counting detector according to claim 1, wherein the generating circuitry comprises
first generating circuitry provided for each of a predetermined number of the capacitors, and that generates a first digital signal by using an accumulation result per predetermined number of the capacitors and first reference information; and
second generating circuitry configured to generate a second digital signal by using the first digital signal generated by the first generating circuitry and second reference information, and that uses the generated second digital signal as the digital signal.

21. An X-ray computed-tomography (CT) apparatus, comprising:
a photon counting detector that comprises
a plurality of X-ray detection elements configured to detect an X-ray and generate an electrical signal;
a plurality of capacitors, each of the plurality of capacitors being connected to a different one of the plurality of X-ray detection elements without an intervening amplifier, and accumulating an electrical signal generated in the one of the plurality of X-ray detection elements, wherein no transistor is connected to each of the plurality of capacitors without an intervening circuit element; and
generating circuitry configured to store reference information, and configured to generate a digital signal by using an accumulation result of the electrical signal in each of the plurality of capacitors, and the reference information;
collecting circuitry configured to collect the digital signal from each of the X-ray detection elements; and
reconstructing circuitry configured to reconstruct an image by using the digital signals collected by the collecting circuitry.

* * * * *

UNITED STATES PATENT AND TRADEMARK OFFICE
CERTIFICATE OF CORRECTION

PATENT NO. : 10,338,012 B2
APPLICATION NO. : 15/446325
DATED : July 2, 2019
INVENTOR(S) : Tooru Kato et al.

Page 1 of 1

It is certified that error appears in the above-identified patent and that said Letters Patent is hereby corrected as shown below:

In the Claims

Column 19, Line 10, Claim 8 change "according to claim" to --according to claim 1,--.

Signed and Sealed this
Eighth Day of October, 2019

Andrei Iancu
*Director of the United States Patent and Trademark Office*